United States Patent [19]

Jaffe

[11] 4,272,398

[45] Jun. 9, 1981

[54] MICROENCAPSULATION PROCESS

[75] Inventor: Howard Jaffe, Gaithersburg, Md.

[73] Assignee: The United States of America as represented by the Secretary of Agriculture, Washington, D.C.

[21] Appl. No.: 49,019

[22] Filed: Jun. 15, 1979

Related U.S. Application Data

[63] Continuation of Ser. No. 934,940, Aug. 17, 1978, abandoned.

[51] Int. Cl.³ .................. B01J 13/02; A01N 25/28
[52] U.S. Cl. .................................. 252/316; 424/19; 424/22; 424/32; 424/78
[58] Field of Search .............. 252/316; 424/19, 22, 424/32, 78

[56] References Cited

U.S. PATENT DOCUMENTS

| | | | |
|---|---|---|---|
| 3,523,906 | 8/1970 | Vrancken et al. | 252/316 |
| 3,773,919 | 11/1973 | Boswell et al. | 424/19 |
| 3,887,699 | 6/1975 | Yolles | 424/19 |
| 3,976,071 | 8/1976 | Sadek | 128/260 |

OTHER PUBLICATIONS

Proceedings, 1977 Controlled Release Pesticide Symposium, Aug. 22-24, 1977, Oregon State Univ.
Sinclair, Environmental Sci. Technol. 1973, 7 (10) 955-956.
Proceedings, 5th Internat'l Symposium on Controlled Release of Bioactive Materials, Aug. 14-16, 1978.
Controlled Release Polymeric Formulations, ACS Symposium Series 33, Amer. Chem. Soc., 1976, Chapter 8.

*Primary Examiner*—Richard D. Lovering
*Attorney, Agent, or Firm*—M. Howard Silverstein; William E. Scott; David G. McConnell

[57] ABSTRACT

Pesticides, insect growth regulators and other substances are encapsulated by dissolving the substance to be encapsulated and a biodegradable polymer in a suitable organic solvent, dispersing the solution in an aqueous medium and stirring until the solvent evaporates to form a matrix of the substance in the polymer.

5 Claims, No Drawings

MICROENCAPSULATION PROCESS

This application is a continuation-in-part of application Ser. No. 934,940, filed Aug. 17, 1978 now abandoned.

BACKGROUND OF THE INVENTION

1. Field of the Invention

This invention relates to a microencapsulation technique and more specifically to a method of encapsulating pesticides and insect growth regulators.

2. State of the Art

Many microencapsulation techniques are known in the art and many of them are described in "Microcapsules and Microencapsulation Techniques," M. H. Gutcho, Noyes Data Corporation, N.J., 1976. The known art which is closest to the subject invention is the following:

1. U.S. Pat. No. 3,523,906. The substance to be encapsulated is emulsified in a solution of a polymeric material in solvent and the solvent is removed by evaporation.
2. U.S. Pat. No. 3,914,402. An ophthalmic antibiotic and an ophthalmic steroid are encapsulated with polylactic acid.
3. U.S. Pat. No. 3,909,444. The material to be encapsulated is dispersed in a mixture of solvent, polymeric capsule wall material, and polyethylene, the mixture heated and then slowly cooled during the cource of which capsules are formed.
4. U.S. Pat. No. 3,557,279. Ethylcellulose, polyethylene granules and indomethacin are dispersed in cyclohexane and heated. The mixture is then allowed to cool during which the ethylcellulose lost solvent and developed into solid encapsulating walls.

SUMMARY OF THE INVENTION

An object of this invention is to provide a means of encapsulating organically soluble pesticides and insect growth regulators and other organic compounds or mixtures of compounds in a biodegradable polymer such as polylactic acid and copolymers of lactic and glycolic acids.

Another object is to provide a means of encapsulating organically soluble pesticides and other substances in a biodegradable polymer so that the encapsulated material is plasticized in the polymer thereby providing a product having only one phase.

A further object is to provide a means of encapsulating organically soluble pesticides and other substances so that the product will provide a uniform release of the encapsulated substance.

A still further object is to provide a means of encapsulating organically soluble pesticides and other substances that will yield a product which will not prematurely release the encapsulated substance if the capsule is ruptured.

Still another object is to provide a microencapsulation technique that can be used to encapsulate any organic compound or mixture of organic compounds or other substance that is soluble in an organic solvent.

According to this invention the above objects are accomplished by a method wherein the pesticide, insect growth regulator or other substance to be encapsulated and a biodegradable polymer are dissolved in a suitable solvent and the solution dispersed in an aqueous medium and stirred until the solvent evaporates and a matrix or solid solution of the pesticides or other substance is formed in the biodegradable polymer. The product is the encapsulated substance plasticized in the polymer.

DETAILED DESCRIPTION OF THE INVENTION

Microencapsulation is a very valuable tool and finds uses in a wide variety of industrial applications. It can be used, inter alia, to keep materials from volatilizing, to protect against oxidation, and to mask an unpleasant odor or taste. However, one of the more interesting uses of microencapsulation is that of providing a means of slowly releasing the encapsulated material over a prolonged period of time. Typically, particles of the material to be encapsulated are coated with the encapsulating material by spray or air suspension techniques or particles of the material are dispersed throughout a solution of the coating material.

While searching for a simple procedure to encapsulate organic compounds or mixtures of organic compounds for pesticidal and other uses, I discovered that I could encapsulate the compound, that is, the active material, by dissolving the compound and a biodegradable polymer in a suitable solvent, dispersing the solution of active material and polymer in an aqueous medium, and stirring the dispersion until the solvent evaporated. In this manner I formed a matrix or solid solution of the active material in the biodegradable polymer, that is, the active material was plasticized in the polymer, thereby providing a one-phase product. This is in contrast to encapsulated materials in general use which are two-phase and consist of a core and shell. In the event of a rupture or cut or some other penetration of a two-phase capsule the active material would be rapidly released. This does not occur when the capsule is one-phase. The aqueous medium consisted of water and a small amount of an anionic surfactant to help maintain the dispersion.

The invention is exemplified in the following examples by the microencapsulation of the pesticides famphur (O-[p-dimethylsulfomoyl phenyl]O, O-dimethyl phosphorothioate) and stirofos (2-chloro-1[2,4,5-trichlorophenyl]vinyl dimethyl phosphate) in poly(lactic acid), the non-persistent insect growth regulator, methoprene [isopropyl (E,E)-11-methoxy-3,7,11-trimethyl-2,4-dodecadienoate], and the insect growth regulator, 2-ethoxy-9(p-isopropylphenyl)-2,6-dimethylnonane.

EXAMPLE 1

1.50 g. poly(d,l-lactic acid) and 1.50 g. stirofos were agitated in a one liter container with 40 ml. methylene chloride until complete solution of the pesticidepolymer mixture was effected. The solution was then dispersed in an aqueous medium containing 450 ml. water and 0.21 g. sodium dodecyl sulfate. The dispersion was stirred with a four-bladed stainless steel impeller (Fisher Catalog No. 14–502-5; however, any similar impeller will suffice) at about 1300–1600 r.p.m. at ambient room temperature of about 18°–22° C. for about one hour until the methylene chloride evaporated and a soapy white suspension was obtained. The suspension was filtered by gravity through fluted filter paper of medium-fine porosity (a smooth surface, low wet strength filter that filters 98% of 8 μm particles at medium flow rate such as Whatman #2), washed copiously with water and then air dried to yield 2.40–2.88 g. of white powder containing aggregates of microparticles. The process described above was repeated eight times and the products combined. All aggregates larger than 595µ were sieved out with a number 30 standard sieve. The remaining aggregates (7.53 g.) were stirred with 600 ml. hexane for five minutes, filtered through fluted filter paper (described above), washed with 150 ml. hexane, and air dried to yield 4.93 g. of white powder containing aggregated microparticles. The powder was sized with numbers 30, 50 and 80 standard sieves as described in J. Pharm. Sci. 65(6), 847, 1976, to yield three samples of aggregated microparticles. The particle size of the three samples of aggregates was as follows: 1. 295–595µ; 2. 177–295µ, and 3. <177µ. The samples contained 42.0%, 31.2%, and 23.6% active material, respectively. Examination of the aggregates by differential interference contrast microscopy showed that the aggregates were made up of generally spherical individual microcapsules having diameters ranging from about 5µ to about 162µ.

EXAMPLE 2

0.57 g. poly (d, l-lactic acid) and 2.25 g. stirofos were dissolved in 40 ml. methylene chloride and processed as described in Example 1 to give 1.99 gm. of white powder. As in Example 1, aggregates larger than 595µ were sieved out to give 1.12 gm. of material which was washed, air dried and sized as in Example 1 to give samples 4–6 having particle size ranges the same as Examples 1–3, respectively. Sample 6 contained 42.6% active material. The amount of active material in Examples 4–5 was not determined.

EXAMPLE 3

1.50 g. poly (L(+)-lactic acid) and 1.50 g. stirofos were dissolved in 40 ml. methylene chloride and processed as described in Example 1 to give 2.42 g. of white powder. As in Example 1, aggregates larger than 595µ were sieved out to give 0.98 g. of material which was washed, air dried and sized as in Example 1 to obtain samples 7–9 having particle size ranges the same as Examples 1–3, respectively. Sample 9 contained 47.4% active material. The amount of active material in Examples 7 and 8 was not determined.

EXAMPLE 4

2.20 g. poly (d,l-lactic acid) and 80 g. famphur were agitated in one liter container with 45 ml. methylene chloride until complete solution of the pesticide-polymer mixture was affected. The solution was then dispersed in an aqueous medium containing 450 ml. water and 0.21 g. sodium dodecyl sulfate. The dispersion was stirred with a four-bladed stainless steel impeller (as in Example 1) at about 1600–1800 r.p.m. at ambient room temperature of about 18°–22° C. for about 0.5 hr. The dispersion was then chilled in an ice water bath and stirred as above for about an additional 1.75 hr. until a soapy white suspension was obtained. The suspension was filtered, washed and dried as in Example 1 to yield 2.30–2.65 g. of white powder. The process was repeated six times and yields combined. All aggregates of microparticles larger than 595µ were sieved out with a number 30 standard sieve. The remaining aggregates (13.92 g.) were sized as in Example 1 to yield three samples, 10–12, with the same ranges of particle sizes as samples 1–3, respectively. Samples 11 and 12 contained 25.5% and 25.7% active material, respectively. The amount of active material in Sample 10 was not determined.

EXAMPLE 5

2.0 g. poly (L(+)-lactic acid) and 1.0 g. famphur were dissolved in 45 ml. methylene chloride and processed as described in Example 4 to yield 2.0 g. of white powder. As in Example 4, aggregates larger than 595µ were sieved out. The remaining particles were sized as in Example 4 to yield three samples, 13–15, with the same ranges of particle sizes as Samples 10–12, respectively. Samples 14 and 15 contained 33.0% and 29.6% active material, respectively. The amount of active material in Sample 13 was not determined.

EXAMPLE 6

0.90 g. poly (d,l-lactic acid) and 0.60 g. methoprene were dissolved in 25 ml. methylene chloride, the solution dispersed in 250 ml. water containing 0.11 g. sodium dodecyl sulfate, the mixture stirred for 5 minutes, then chilled in a ice-water bath while stirring was continued for a total of two hours to yield 0.94 g. of a coarse powder made up of aggregates of microcapsules containing 40.0% active materials. Two additional runs of the above process yielded microcapsules containing 33.3% and 26.5% active material, respectively, in poly (d,l-lactic acid). In addition, individual samples of microcapsules containing 33.3% and 26.5% active material, respectively, in a copolymer of 90% poly (L(+)-lactic acid) and 10% poly (glycolic acid) were prepared by the same process.

EXAMPLE 7

2-ethoxy-9(p-isopropylphenyl)-2,6-dimethylnonane was encapsulated by the process described above. Individual samples of microcapsules containing 28.2% and 33.4% active material, respectively, in poly (d,l-lactic acid) were prepared.

The various microencapsulated products obtained in Examples 1–7, above, were analyzed for percent active material by ultraviolet and infrared spectroscopic techniques as described in the Proceedings, 1977 Controlled Release Pesticide Symposium, August 22–24, 1977. As also described in the Proceedings, the microencapsulated stirofos and famphur, formulated as suspensions in oil, are useful as systemic pesticides against ticks. As described in the proceedings, 5th International Symposium on Controlled Release of Bioactive Materials, August 14–16, 1978, methoprene is an effective agent against common cattle grub. The 1977 and 1978 Proceedings are hereby considered incorporated by reference into this specification. 2-ethoxy-9(p-isopropylphenyl)-2,6-dimethylnonane is also effected against common cattle grub. The methoprene and the 2-ethoxy-9(p-isopropylphenyl)-2,6-dimethylnonane were not formulated as suspensions in oil. Individual gelatin capsules were loaded with microcapsules of the desired compound and the gelatin capsules were implanted underneath the skin, usually in the ear, of the animal being used for testing purposes.

Although the process of this invention has been exemplified with four compounds, two of which are known pesticides and two of which are known insect growth regulators, the process is applicable to other compounds and substances which are soluble in volatile organic solvents. Since the purpose of the volatile organic solvent such as methylene chloride is to solubilize the substance to be encapsulated and the biodegradable polymer prior to dispersing the solution in the aqueous medium, any volatile organic solvent in which both substances are soluble is operable and suitable in the process of this invention.

I claim:

1. A process for one-phase encapsulation of organic compounds selected from the group consisting of famphur and stirofos systemic tick pesticides for oil suspension formulations and of methoprene and 2-ethoxy-9(p-isopropylphenyl)-2,6-dimethylnonane insect growth regulators comprising dissolving said compound and a biodegradable polymer selected from the group consisting of polylactic acid and copolymers of lactic and glycolic acids in methylene chloride, agitating until complete solution of the compound-polymer mixture is affected, dispersing said solution in an aqueous medium containing an anionic surfactant, and stirring said dispersion until the solvent evaporates, thereby forming a soapy white suspension of said compound in said polymer, filtering, washing, drying and sizing to white powder one-phase particles.

2. An encapsulation process for one-phase encapsulation of compounds and mixtures of compounds soluble in volatile organic solvents comprising dissolving said compound and a biodegradable polymer selected from the group consisting of polylactic acid and copolymers of lactic and glycolic acids in a suitable organic solvent, dispersing the solution in an aqueous medium containing an anionic surfactant, and stirring said dispersion until the solvent evaporates, thereby forming a soapy white suspension of said compound in said polymer, filtering, washing, drying and sizing to aggregates of one-phase particles.

3. The process of claim 2 wherein said aggregates have a particle size of from about $177\mu$ to $595\mu$.

4. The process of claim 3 wherein the aggregates are formed of individual, generally spherical-shaped microcapsules, said microcapsules having diameters of from about $5\mu$ to $162\mu$.

5. The process of claim 4 wherein said microcapsules contain from about 23.6 to 47.4% active material.

* * * * *